US005702708A

United States Patent [19]
Ellis

[11] Patent Number: 5,702,708
[45] Date of Patent: Dec. 30, 1997

[54] SALMONICIDA IRON REGULATED PROTEIN AND LIPOPOLYSACCHARIDE VACCINE

[75] Inventor: Anthony E. Ellis, Aberdeen, Scotland

[73] Assignee: The Secretary of State for Scotland in Her Britannic Majesty's Government of the United Kingdom of Great Britain and Northern Ireland, London, England

[21] Appl. No.: 157,154

[22] PCT Filed: Jun. 5, 1992

[86] PCT No.: PCT/GB92/01016

§ 371 Date: Jan. 4, 1994

§ 102(e) Date: Jan. 4, 1994

[87] PCT Pub. No.: WO92/21370

PCT Pub. Date: Dec. 10, 1992

[30] Foreign Application Priority Data

Jun. 7, 1991 [GB] United Kingdom .................. 9112310

[51] Int. Cl.$^6$ ............. A61K 39/106; A61K 39/02; A61K 39/00; A01N 63/00
[52] U.S. Cl. ............. 424/261.1; 424/93.1; 424/184.1; 424/234.1; 424/236.1; 424/191.1; 424/203.1; 424/201.1
[58] Field of Search ............. 424/184.1, 261.1, 424/93.1, 234.1, 191.1, 203.1, 201.1

[56] References Cited

FOREIGN PATENT DOCUMENTS 8202491  8/1982  WIPO ................. A21K 39/02

OTHER PUBLICATIONS

Chant et al. Journal of Bod 156: 758–764, 1983.
Aoki et al. FEMS Microbiology 27: 299–305, 1985.
Evenberg et al. Biochem Biophip Acta 815: 233–244, 1985, Abstract.
Massad et al. Abstracts of the 90th Am. Meeting of the ASM p. 42: Abstract 13–95.
Austin et al. from Bacterial Fish Palkozes Chapter 9, includes pp. 170 & 177, 1957.
Gilleland et al. EVR J. Clin Microb 6: 231–233, 1987.
Chant et al. Journ. of Bact 156: 758–764, 1983.
Aoki et al. FEMS Microb 27: 299–305, 1985.

*Primary Examiner*—Hazel F. Sidberry
*Attorney, Agent, or Firm*—Nixon & Vanderhye P.C.

[57] ABSTRACT

A treatment of fish for infection by the organism *Aeromonas salmonicida* using either one or both of two components produced by a culture of the organism. The culture is treated to kill the organisms prior to use, preferably by treatment with formalin after the components have been produced. One of the components, only produced when the culture is grown under iron limiting conditions induces production of antibodies which cause death of the organisms when injected intraperitoneally into fish.

8 Claims, No Drawings

SALMONICIDA IRON REGULATED PROTEIN AND LIPOPOLYSACCHARIDE VACCINE

The present invention relates to use of known and novel agents as vaccines or medicaments for the prophylactic and therapeutic treatment of fish, inter alia salmon, trout and carp, for *Aeromonas salmonicida* (*A. salmonicida*) infection.

*A. salmonicida* is a pathogen of some significance, particularly in activities such as fish farming, due to its causation of the systemic disease furunculosis (Herman, R. L. (1968) Fish furunculosis 1952–66. Trans. Amer. Fish. Soc. 97:221–230). Acute forms of this disease are associated with rapid growth of the organism in the major body organs which produces a terminal septicemia frequently accompanied by severe tissue necrosis. The organism is particularly known for its effects on the *salmonidae* but is capable of infecting a wide range of fish species. Further significant economic effects of the organism include its ability to induce erythrodermatitis disease in carp. Intramuscular injection of as few as 100 virulent cells can produce death within 9 hours and as asymptomatic carriers can die of fulminant furunculosis if subjected to environmental stress it is desirable to vaccinate fish as opposed to attempting curative treatments.

It is known that fish produce antibodies to both virulent and non-virulent *A. salmonicida* cells or their extracellular products (ECP) but it is found that direct production of antibodies by administration of these antigens to coho salmon provides less effective protection than administration of rabbit raised antisera. It appears that rabbits are more efficient than fish in responding to protective antigens (Olivier et al, (1985) J. Fish Dis., 8:43–55) but in any case the nature of these antigens (immunogens) has not as yet been determined.

Further work has demonstrated that while the majority of formalinised *A. salmonicida* ECP antigens are immunogenic in rabbits, most, including the protease and the haemolysin, were not detectably immunogenic in rainbow trout (Hastings et al, (1988). J. Fish. Dis., 11:309–323). Suspicion that the extracellular protease component of ECPs is an important factor in virulence and growth led to investigation of these as possible specific immunogenic antigens (Hastings et al, (1988), Aquaculture, 70:207–218). These studies showed that it is possible to provide some protection by use of rabbit antisera containing antibodies to said protease, antisera to strains deficient in protease having marginal protective effect.

It has been shown that rabbit antisera to *A. salmonicida* are incapable of activating fish complement in rainbow trout (Sakai et al, (1981) Bull. Jpn. Soc. Sci. Fish., 47:979–991) so cannot kill the bacteria or act as opsonins, presumably only being capable of neutralizing the biological effects of their toxins. The level of protection and its duration in such 'passively' immunized fish depends on the rate at which the rabbit antibodies are complexed by the bacterial antigens released in the fish. The present inventor and coworkers have found that rabbit antisera monospecific to extracellular protease do not provide passive protection. (K K Lee—thesis (1990) Aberdeen University—'Studies on the extracellular lethal factors of *A. salmonicida* in Atlantic salmon').

Some success has been obtained by workers who have emulsified a specific chromatographic fraction of *A. salmonicida* extracellular product in Freund's incomplete adjuvant and injected this intraperitoneally into brook trout (Cipriano et al, (1985), Can. J. Fish. Aquat. Sci. 42. 1290–1294). However, trout injected with this fraction only were not protected. Further analysis shows the fraction to contain lipopolysaccharide (LPS), as does the organism's endotoxin, and electrophoresis shows the fraction and endotoxin to comprise similar mixtures of proteins although non-protein material is also present. It should be noted that the extracellular product used here was from 96 hour old cultures and was thought to contain large amounts of cell wall LPS. These results are consistent with those previously obtained with whole bacterial cell preparations in adjuvant (Krantz et al, (1964), Prog. Fish-Cult. 26:3–10).

The present inventor has found biological and chemical differences between external LPS (ELPS), herein defined as that obtained from the extracellular fluids derived from cell free culture supernatant, and that obtained from *A. salmonicida* cell wall fractions (CWLPS). These include differences in haemolytic activity, fatty acid methyl ester and sugar composition. It has further been determined, surprisingly, that ELPS from cultures of the bacteria, without adjuvant, provides relative percent survival (RPS) values in excess of 65% when doses of 100 µg and over are injected into fish in 0.1 ml volume. Injection of doses of 50 µg or less fails to protect thus doses of over 50 µg (500 µg/ml×0.1 ml=50 µg/fish) are determined as necessary to provide a protective response. The optimal dose is around 200 µg/fish.

These intraperitoneal doses of external LPS (ELPS) which are required to induce protection are well in excess of those present in crude broth cultures and in existing commercial vaccines and the humoral and protective response is found to be dose dependent.

The present inventor has provided a still more efficacious vaccine agent which is further capable of inducing antibodies that actually kill *A. salmonicida* bacteria; this is of some significance, as this organism is notoriously resistant to serum antibody killing. This agent comprises outer membrane protein (OMP) components produced by *A. salmonicida* cultured under iron limiting conditions.

Iron limiting culture conditions are those in which the amount of iron available to the bacteria in the culture is less than that which is required for normal growth and can be brought about by not including sufficient in the media or by including therein chelating agents which reduce its availability. The sub-culture of organisms several times in such media before production conveniently depletes iron stores.

It is established that bacteria have an absolute requirement for iron and that *A. salmonicida* is typical in this respect. It has further been shown that *A. salmonicida* is induced to produce such OMPs in iron limiting conditions (Chart and Trust, (1983). J. Bacteriol., 156:758–764). These iron regulated OMPs (IROMPS) have been characterised using electrophoresis and may be isolated by various standard techniques such as eg. electrophoresis and/or centrifugation (Aoki and Holland, (1985). FEMS Microbiol. Lett. 27:299–305).

Despite their existence and isolation having been reported neither the suitability of these or related OMPs as vaccine active components or their respective antibodies as therapeutic, bactericidal agents for treating fish for furunculosis infection has been suggested. Where iron regulated OMPs have been prepared for vaccine screening purposes they have not been proved effective (Evenburg et al, (1988) J. Fish Diseases, Vol 11, pp337–349). In this regard it is to be noted that these OMPs were apparently not those identified in the present application as the culture in which they were prepared contained what the present inventor has found to be insufficient iron-chelating compound (10 µM 2,2'-dipyridyl) to evoke IROMPs production.

The present invention thus provides a first aspect which comprises the use of iron regulated outer membrane proteins (IROMPs) of *A. salmonicida*, defined herein as the outer membrane proteins (OMP) derivable from *A. salmonicida* organisms which have been cultured in iron-limited conditions but not found when such organisms are cultured in iron replete conditions, as vaccine active component or medicament for prophylaxis and/or therapy of *A. salmonicida* evoked disease.

In order that a man skilled in the art may more readily determine particularly suited forms for administration of the iron limited (regulated) OMPs (IROMPs) in the use of the present invention, compositions containing the IROMPs are also provided and form a second aspect of the invention together with methods for their preparation.

A third aspect of the present invention provides the use of antibodies, raised in fish or other animals, to IROMPS and/or ELPS, and compositions containing these antibodies, as medicaments for the prophylactic and/or therapeutic treatment of *A. salmonicida* evoked disease. A fourth aspect of the invention provides these antibodies and compositions per se, eg. in physiologically acceptable carrier such as aqueous carriers, particularly antisera themselves and affinity purified antibodies from these antisera resuspended in such aqueous carriers.

A fifth aspect of the present invention comprises the use of external lipopolysaccharide (ELPS) (as defined herein), obtained from the supernatant fluid of a culture of *A. salmonicida*, in an amount sufficient to evoke an immune response when administered to fish without adjuvant, as a medicament for the prophylactic treatment of *A. salmonicida* evoked disease. This aspect is related to the other aspects of the invention in so far as both ELPS and IROMPs components are necessary for the medicament for the prophylaxis of *A. salmonicida* evoked diseases (ie. *A. salmonicida* vaccines) to be maximally effective. It is clear that these components might be administered separately but within a given time frame so as to achieve the desired maximal effect. As they are part of the same inventive concept, ie. a vaccine for *A. salmonicida*, they are referred to here as separate components within the same invention and claimed as such.

A sixth aspect of the present invention provides compositions comprising said *A. salmonicida* ELPS in an amount sufficient for said use and further provides methods for its preparation. Such compositions conveniently comprise more than 0.5 mg/ml ELPS such that 0.1 ml of a liquid composition may provide sufficient ELPS to produce an immune response. Preferred amounts for such composition are 1 mg/ml or more, more preferably 2 mg/ml or more.

A seventh aspect of the present invention provides vaccine use of a preferred composition comprising both IROMPs and ELPS components and a eighth aspect provides compositions suitable for administration in that use and methods for preparation of such compositions.

Particularly provided are 'dosage units' of such compositions of IROMPs, ELPS and IROMPs/ELPS combination compositions. The term dosage unit relates to formulations of the compositions which are suitable for administration to animals to be vaccinated or therapeutically treated. Particularly envisaged as such dosage units are ampules of liquid vaccine composition, pellets, tablets, capsules, implants etc as are known to be suitable for administering agents to fish. In the case of pellets a large number may be required to adminster the necessary dosage while several fish may be treated by i.p. injection with eg. 0.1 ml doses from a single 5 ml ampule. In this respect it is envisaged that the term 'number of dosage units' as used in the claims herewith may be less than one. For a 5 ml ampule thus a 0.1 ml dose may be administered in 0.02 of a dosage unit. For a 1 ug IROMPs pellet however 20 dosage units (the pellets) may be required. The essential feature of these dosage units is that a physiologically acceptable number of units for a single administration should contain enough vaccine component.

The IROMPs component may be used in isolated form but can be conveniently used in whole membrane form such as in formalinised whole membrane or whole outer membrane fractions derived from an iron-restricted culture or, more conveniently, formalinised whole cells from such culture. The iron restriction culture medium comprises any medium known to be suitable for growth or support of *A. salmonicida* organisms in which the iron component has been omitted or reduced to below levels necessary for normal growth or to which iron limiting agents have been added. Suitable iron limiting agents are chelating agents such as eg. EDTA, EDDA and dipyridyl and use of these is particularly preferred due to their ability to deplete internal iron stores in the organisms and thus stimulate iron seeking mechanisms associated with the IROMPs components. In this regard it should be noted that 2,2'-dipyridyl levels of 10 μM are insufficient. Preferably 100 mg/ml EDDA or 100 μM 2,2'-dipyridyl is included.

A typical IROMPs culture is carried out for 24 hours to 72 hours before carrying out inactivation of cells with formalin or other bactericidal treatment or isolation of the IROMPs component. Cultures are conveniently carried out at approximately ambient temperature and are preferably fermented aerobically at constant pH.

In a preferred procedure a sub-culture of *A. salmonicida* is first grown in an iron-chelating agent containing medium for about 24 hours at ambient temperature (eg.22° C.), preferably with shaking, after which it is used to inoculate a fermentation vessel containing the same growth medium in which the bacterium is then grown for approximately 48 hours (2 days), again at ambient temperature, under aerobic conditions and at constant pH (eg. pH 7.0). The culture is inactivated after the 48 hour period and a suitable concentration of cells produced as determined by measurement of the amount of cells expressing IROMPS.

Using the preferred procedure described above a suitable concentration of cells may be conveniently obtained by centrifuging aliquots of the inactivated culture and adding sedimented cells back into a volume of the supernatant until the desired concentration is obtained. Using a typical avirulent *A. salmonicida* strain a cell concentration of between $10^7$ and $10^9$/ml is sufficient to evoke an immunogenic response when injected intraperitoneally in 0.1 ml volume per fish.

This preferred procedure is particularly convenient as it provides both IROMPs and ELPS components in one culture. A particularly advantageous feature of this procedure is that the ELPS component in the supernatant is not reduced when the sedimented cells are added. Thus where both components are provided in the same culture in this way it should be ensured that the ELPS level is allowed to reach its effective concentration before the culture is stopped. It is found that use of 0.1 ml of the $1\times10^7$ cell/ml supernatant produced as above is sufficient to protect fish when injected intraperitoneally (i.p.) although other volume/dilution combinations giving sufficient cells/fish will be suitable. In this regard it is found that i.p. administration of 20 μg/fish of isolated IROMPs component as described herein is sufficient to produce bactericidal antisera. However the vaccines of the present invention have been determined as active when administered in other ways, for example, by immersion of fish in vaccine or by administration in oral delivery forms, eg in capsules.

It will be realised that for the purpose of treating established A. salmonicida infection that the IROMPs and/or ELPS antibodies of the invention will be most effective as they do not have the attendent delay in effect that use of antigen will have due to immune response time. IROMPs antibodies also have the advantage of being bactericidal.

The production of the vaccine/therapeutic components and vaccines/therapeutic compositions of the present invention and the effectiveness of the compositions of the present invention as medicaments for prophylaxis and therapy of furunculosis will now be described by way of illustration only by reference to the following Examples and test results.

EXAMPLE 1

Purified ELPS—Comparison to Cell Wall LPS (CWLPS)

Purified ELPS was prepared from cell free extracellular products of a strain of A. salmonicida using the method of Westphal and Jann (Methods in carbohydrate chemistry (1965) 5 p83–91 and its chemistry compared to that of LPS isolated from A. salmonicida cell walls (TABLE I). The % weight values given are approximate and are provided in order to aid the skilled worker in identifying the ELPS component in culture supernatants. To avoid increase in CWLPS relatively young cultures should be used, eg. less than 96 hours old.

TABLE I

| ELPS Sugar | % wt (anhydrous) | CWLPS Sugar | % wt (anhydrous) |
|---|---|---|---|
| Mannose | 13.97 | Fucose | 7.56 |
| Galactose | 2.57 | Ribose | 7.58 |
| Glucose | 1.59 | Xylose | 0.18 |
|  |  | Mannose | 0.55 |
|  |  | Galactose | 0.85 |
|  |  | Glucose | 6.44 |

These figures correspond to the ELPS sugar component comprising 77% mannose with CWLPS having a sugar component composition of 32.6% fucose, 32.7% ribose and 27.8% glucose; all in % anhydrous weight. Lipid determination of both fractions gave approximate figures of 14.8% weight lipid for ELPS and 49.5% weight lipid for CWLPS.

Comparison of Immunogenic Activity of ELPS with CWLPS

Salmon parr were vaccinated intraperitoneally with 0.1 ml of vaccine comprising 2 mg/ml of either ELPS (EXAMPLE 1) or CWLPS in phosphate buffered saline. Control fish received 0.1 ml of Dulbecco's phosphate buffered saline.

Fish were maintained at 14° C. for 6 weeks post vaccination, a subsample was bled and the serum assayed for antibodies to ELPS or CWLPS. After 6 weeks fish were challenged with a more virulent heterologous strain of A. salmonicida and the mortality of each group monitored; relative percent survival (RPS) was then calculated (TABLE II).

TABLE II

| Treatment | ELPS | CWSLPS | CONTROLS |
|---|---|---|---|
| No. Fish | 401 | 202 | 350 |
| RPS | 55.0 | 29.25 | — |

Control mortality was 77% p = 0.05 by students t test.

Thus a different and superior effect of ELPS in producing a protective response in vaccinated fish thus is clearly demonstrated. Cross absorption studies on the antisera produced on vaccination with each of the two LPSs evidences a difference in epitopic structure of these antigens.

EXAMPLE 2

IROMPs of A. Salmonicida

IROMPs were prepared by harvesting cells from a 500 ml Tryptone Soya Broth (TSB)/100 μM 2,2'-dipyridyl A. salmonicida culture by centrifugation (8000 g for 30 minutes at 4° C.), washed with 20 mM Tris(hydroxymethyl) -methylamine (TrisHCl, pH7.2) resuspended in 20 mM Tris-HCl, 10 mM EDTA (pH7.2) containing 0.1 μg DNase and 0.1 μg RNase per ml and phenylmethylsulphonyl fluoride (PMSF;50 μgml$^{-1}$) and sonicated on ice (6×30 s). Whole cells and debris were removed by centrifugation (20000 g for 20 minutes at 4° C.). Inner membranes were solubilised by addition of Sarkosyl (sodium N-lauryl sarcosinate) to 1.5% (v/v) and incubated for 30 minutes at 22° C. Sarkosyl-insoluble IROMPs were collected by centrifugation at 100,000 g for 1 hour at 4° C., washed and suspended in 20 mM Tris-HCl and stored at −20° C.

The IROMPs containing fractions produced were analysed by the method of Bradford (Analytical Biochem. (1976) 72, 248–254) using phenol-sulphuric acid method/glucose standard of Dubois ((analytical Chem. (1956) 28 350–356) for carbohydrate determination, several LPS tests and the thiobarbiturate 2-keto-3-deoxyoctonate (KDO) test. All

TABLE III

| OMP Antigen | Protein μg/ml | LPS μg/ml | LAL EUml$^{-1}$ | KDO μg/ml LPS/mg protein | Carbohydrate mg/ml |
|---|---|---|---|---|---|
| Avirulent Iron-replete | 200 | 230 | >268 | 5.5 | 4.3 |
| Avirulent IROMPs | 200 | 285 | >268 | 5.0 | 9.0 |
| Virulent IROMPs | 200 | 52.2 | >268 | 0.2 | 0.38 | confirmed their status as OMPs. At the concentration of 200 μg/ml IROMPs high levels of LPS and carbohydrate were detected although A-layer proficient (virulent) strains had less due to the additional protein. (See TABLE III). Protein concentrations were standardised in each case prior to calculation of other variables.

Comparison of IROMPS From Variety of strains of A. Salmonicida

To determine effect of iron-restriction on the OMPs of A. salmonicida in general, 18 typical strains and 2 atypical strains were grown on TSB containing EDDA (100 mg/ml) and the OMPs produced were compared by SDS-PAGE with those from organisms grown in TSB alone and TSB/EDDA plus FeCl$_3$ (0.54 mM). Growth under iron restricted conditions resulted in expression of four novel OMPs (IROMPs) of apparent molecular weight 82, 77, 72 and 70 kDa which were not present in cultures of those strains grown under iron-replete conditions (TSB or TSB+EDDA+FeCl$_3$).

Culture of A. salmonicida was carried out under varying conditions to check that disadvantageous temperatures or oxygenation levels does not induce IROMPS production under iron replete conditions. Use of 15° C., 22° C. and anaerobic conditions did not in themselves result in expression of the IROMPs. Use of 2,2'-dipyridyl (100 μM) in place of EDDA however produced identical IROMPs but in quantatively greater amounts, thus indicating this chelator to be preferred. Studies on IROMPs cross-reactivity with salmon antisera and monospecific rabbit anti-IROMP antiserum raised to IROMPs of a single strain and all showed staining using Western blotting techniques.

SDS-PAGE analysis of OMP vaccines indicates that the only difference between iron-replete and iron-restricted OMPs fraction is the presence of the 82, 77, 72 and 70 kDa IROMPs.

EXAMPLE 3

IROMPS Antibodies/Compositions—Passive Immunisation

A salmon antiserum raised against a mixture of IROMPs from two typical *A. salmonicida* strains grown under iron restricted conditions and shown to contain antibodies directed against the IROMPs by use of Western blotting techniques was used to passively immunise Atlantic salmon against bath challenge exposure to a virulent strain whereon an RPS of 77% was produced.

To ensure that IROMPs were responsible for the aforementioned RPS monospecific anti-IROMP antiserum prepared in rabbit against the gel-isolated IROMPs of the typical strain was also evaluated for its ability to passively immunise against a heterologous bath challenge whereon 55% RPS was achieved. Affinity purified IgG from the rabbit antiserum further gave an RPS of 83%.

EXAMPLE 4

Bactericidal Activity of Immune Sera

Antisera was produced by injecting salmon intraperitoneally with a mixture of equal amounts of IROMPs of two typical *A. salmonicida* grown under iron-restricted conditions in combination with Freunds Complete Adjuvant. Three typical strains and one atypical strain of *A. salmonicida* were used to determine their abilty to grow in-vitro in heat-inactivated normal fish serum; all strains examined proved capable of doing so. An avirulent strain, capable of producing IROMPs (as are all strains so far tested) was not capable of growth in such serum when complement was present though the virulent strains were.

In contrast salmon anti-IROMPs serum plus complement was found to be bactericidal with 45 to 84% of organisms being killed in the time alotted to assay. When the complement source was heat inactivated the bactericidal activity was reduced to 15 to 20% of organisms being killed. Selective adsorption of the antibodies showed the bactericidal activity to reside completely with the IROMPs. Similar adsorption with rabbit antisera also confirmed this and rabbit antisera plus complement was bactericidal for 63 to 85% organisms as opposed to 15 to 60% with heat treated complement.

EXAMPLE 5

Isolated IROMPs Active Immunisation of Salmon

Altantic salmon parr (about 8 to 10 g) were held in fresh water tanks supplied with fresh heated running water, this being supplied from a local loch and heated to 14° C. Fish were anaesthetised with ethyl p-aminobenzoate during immunisation and each was injected intraperitoneally with 0.1 ml PBS containing 20 μg of IROMPs as produced above. Forty two days post-immunisation fish were subjected to a 24 hour bath challenge exposure of approximately $1 \times 10^5$ cfu of a virulent strain of *A. salmonicida* and mortalities recorded daily. RPS values of 36.9% (heterologous challenge) and 55% (homologous challenge) to 100% were achieved as compared to controls on challenge with *A. salmonicida* strains.

EXAMPLE 6

Fish and Non-Fish Origin Antisera Produced From IROMPS

Altantic salmon parr (about 8 to 10 g) were held in fresh water tanks supplied with fresh running water at 18° C. and were immunised intraperitoneally with 100 μl salmon anti-IROMPs sera, rabbit anti-IROMPs sera or 50 μl affinity column purified rabbit anti-IROMP IgG, the latter two including normal rabbit serum (SAPU) as a source of complement. IgG was purified on an Immunopure A/G column. Forty two days post-immunisation fish were subjected to a 24 hour bath challenge exposure of approximately $1 \times 10^5$ cfu of a virulent strain of *A. salmonicida* and mortalities recorded daily. Infection with organism was confirmed in mortalities by standard methods (TABLE V).

TABLE V

| Treatment | No. fish | % Mort | RPS v PBS Control | RPS v serum Control |
|---|---|---|---|---|
| PBS | 20 | 40 | | |
| NSS 100 μl | 7 | 43 | –7.5 | — |
| ISS 100 μl | 10 | 10 | 75 | 77 |
| NRS 100 μl | 20 | 20 | 50 | — |
| IRS 100 μl | 20 | 10 | 75 | 50 |
| NRIgG 50 μl | 20 | 30 | 25 | — |
| IRIgG 50 μl | 20 | 5 | 88 | 83 |

N = normal; I = immune; SS = salmon serum; RS = rabbit serum; RIgG = rabbit IgG + NRS for complement; all doses in μl are per fish.

EXAMPLE 7

Combined IROMPs and ELPS Vaccine

An A layer non-proficient (lacking) *A. salmonicida* strain stored in Tryptone Soy Broth (TSB) and glycerol in liquid nitrogen immersed vessels was aliquoted onto Tryprone Soy Agar (TSB plus 1.5% w/v agar, (TSA) Oxoid Ltd) containing either 100 mg/l ethylenediamine di-(o-hydroxyphenylacetic acid) (EDDA) or 100 μM 2,2-dipyridyl (Sigma) for the purposes of limiting the availability of iron by, inter alia, reducing internal iron stores.

A sub-culture of the above treated organism was grown for 24 hours at 22° C. in 100 ml of TSB containing the same concentration of EDDA or 2,2 dipyridyl as above, the medium being shaken over this period. This sub-culture was used to inoculate further such growth medium in a fermentation vessel which was then cultured for 48 hours at 22° C. under aerobic conditions at a constant pH 7.0 using 2M $H_3PO_4$ and 2M NaOH as titrants. The resulting culture was inactivated by the addition of 0.5% formalin (40% formaldehyde in water).

Analysis shows that the IROMPs component contained at least four additional outer membrane proteins over those produced under iron sufficient conditions. The number of cells per ml of culture medium was adjusted to $1 \times 10^8$ by centrifugation of the culture and addition of cells back into the supernatant, thus maintaining desired cell and ELPS levels and providing a combination vaccine. NB:Although this method is exemplified with non-virulent A-layer lacking strain it is equally applicable to IROMPs production from virulent A-layer proficient strains.

Efficacy studies: A variety of concentrations of ELPS, inactivated IROMPS induced cells and combinations of the two were injected intraperitoneally into fish in 0.1 ml volumes, the fish exposed to *A. salmonicida* and the Relative Percent Survival was determined. The results of this study are given in Table VI below.

TABLE IV

| AGENT | Dose/fish | fish | % mortality | RPS |
|---|---|---|---|---|
| None | | 45 | 80 | |
| ELPS | 200 µg | 45 | 24.4 | 70 |
| | 400 µg | 45 | 28.8 | 64 |
| | 600 µg | 45 | 17.7 | 78 |
| IROMPs | $10^6$ | 45 | 6.6 | 92 |
| cells | $10^7$ | 45 | 8.8 | 89 |
| | $10^8$ | 45 | 24.4 | 70 |
| IROMPs | $10^7$/200 µg | 45 | 2.2 | 97 |
| cells/ | $10^7$/400 µg | 45 | 15.3 | 81 |
| ELPS | $10^7$/600 µg | 45 | 0 | 100 |

Note: ELPS and IROMPS concentration in vaccine solution (the culture supernatant in the case of ELPS and IROMPs cells/ELPS) is 10 × that in the dose per fish; in all cases vaccine solution is given as 0.1 ml per fish.

It can be seen from the results afforded by ELPS alone that the dose required to induce protection is well in excess of that which is present in crude broth supernatants and existing commercial vaccines. It is essential that ELPS rather than cell wall derived LPS is used, the latter being associated with postulated lysis product in older cultures. To ensure ELPS is being used it is recommended that cultures less than 96 hours old are used. As stated above, the IROMPs cell component provides a bactericidal immunogenic response as well as a protective response. In this trial neither component provided complete protection on its own but a combination vaccine is demonstrated to provide 100% RPS. It has been shown however (see IROMPs examples above) that in certain combinations of immunising strain/challenge strain that 100% RPS may be achieved with IROMPs alone.

Temperature Effects

The temperature of use of the 'active' IROMPs vaccines of the present invention is critical. Vaccination at 4.5 and 6.5° C. was shown to produce a far slower immune response than vaccination at eg. 11° to 14° C. in studies carried out by the methods used above. Thus while vaccination at these lower temperatures will meet with at least some degree of success it cannot be ensure that antibody titres will be high enough to resist a challenge until some time after the ambient temperature has been elevated. It is thus a sensible precaution that heated water is used during the vaccination process or that an additional agent, eg. adjuvant, is used where low temperature is a problem.

I claim:

1. A method of protecting fish from or treating fish having an *Aeromonas salmonicida* evoked disease comprising administering to said fish an effective amount of iron regulated outer membrane proteins as a vaccine active component.

2. A method of protecting fish from or treating fish having an *Aeromonas salmonicida* evoked disease comprising administering to said fish an effective amount of iron regulated outer membrane proteins and external lypolysaccharides as a vaccine active component.

3. A composition comprising iron regulated outer membrane proteins of *Aeromonas salmonicida* and adjuvant in a form suitable for administration to an animal body for raising antibodies to said iron regulated outer membrane proteins without causing infection with that organism.

4. A composition as claimed in claim 3 wherein the iron regulated outer membrane proteins are in the form of isolated iron regulated outer membrane proteins together with a physiologically acceptable carrier.

5. A composition comprising iron regulated outer membrane proteins of *Aeromonas salmonicida* in a form suitable for administration to an animal body for raising antibodies to said iron regulated outer membrane proteins without causing an infection with that organism, wherein the iron regulated outer membrane proteins are in the form selected from the group consisting of an inactivated whole cell membranes, inactivated whole cell outer membranes and inactivated whole cells.

6. A composition as claimed in claim 3 wherein the inactivated membranes or cells are formalinized.

7. A composition as claimed in claim 3 in dosage unit form comprising, per dosage unit, 24 µg or more iron regulated outer membrane proteins in a physiologically acceptable volume.

8. A composition as claimed in claim 5 in dosage unit form comprising, per dosage unit, $10^6$ to $10^8$ inactivated whole cells in a physiologically acceptable volume.

* * * * *